US008371832B2

(12) United States Patent
Rotem et al.

(10) Patent No.: US 8,371,832 B2
(45) Date of Patent: Feb. 12, 2013

(54) PERISTALTIC PUMP WITH LINEAR FLOW CONTROL

(75) Inventors: Shachar Rotem, D. N. Hefer (IL); Meged Offer, Netanya (IL)

(73) Assignee: Q-Core Medical Ltd., Petach Tikva (IL)

( * ) Notice: Subject to any disclaimer, the term of this patent is extended or adjusted under 35 U.S.C. 154(b) by 461 days.

(21) Appl. No.: 12/644,026

(22) Filed: Dec. 22, 2009

(65) Prior Publication Data
US 2011/0152831 A1   Jun. 23, 2011

(51) Int. Cl.
*F04B 43/12*   (2006.01)
(52) U.S. Cl. .................................... 417/477.7
(58) Field of Classification Search .................. 604/131, 604/151, 216, 506; 417/474, 477.7
See application file for complete search history.

(56) References Cited

U.S. PATENT DOCUMENTS

| | | |
|---|---|---|
| 2,056,322 A | 10/1936 | Hoppe |
| 2,743,898 A | 5/1956 | King |
| 3,443,585 A | 5/1969 | Reinicke |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,236,880 A | 12/1980 | Archibald et al. |
| 4,270,532 A | 6/1981 | Franetzki et al. |
| 4,320,781 A | 3/1982 | Bouvet et al. |
| 4,450,375 A | 5/1984 | Siegal |
| 4,489,863 A | 12/1984 | Horchos et al. |
| 4,682,135 A | 7/1987 | Yamakawa |
| 4,728,265 A * | 3/1988 | Cannon ..................... 417/363 |
| 4,741,736 A * | 5/1988 | Brown ........................ 604/134 |
| 4,755,168 A * | 7/1988 | Romanelli et al. ............. 604/34 |
| 4,893,991 A * | 1/1990 | Heminway et al. ............. 417/53 |
| 4,978,335 A | 12/1990 | Arthur, III |
| 5,096,385 A | 3/1992 | Georgi et al. |
| 5,103,211 A * | 4/1992 | Daoud et al. ................. 340/608 |

(Continued)

FOREIGN PATENT DOCUMENTS

| | | |
|---|---|---|
| DE | 10118086 A | 7/2002 |
| EP | 0215249 A1 | 3/1987 |

(Continued)

OTHER PUBLICATIONS

U.S. Appl. No. 10/535,103 Official Action dated Feb. 2, 2009.

(Continued)

*Primary Examiner* — Nicholas Lucchesi
*Assistant Examiner* — Diva K Chander
(74) *Attorney, Agent, or Firm* — Vladimir Sherman; Professional Patent Solutions

(57) ABSTRACT

A peristaltic pump includes a conduit having a first end for receiving a fluid from a reservoir and a second end for delivering the fluid. A plurality of fingers are disposed at respective locations along a segment of the conduit and are configured to alternately compress and release the conduit at the locations. A cyclical pump mechanism is coupled to move the fingers between respective compressed and released positions in a spatio-temporal pattern so as to drive a predetermined quantity of the fluid through the segment of the conduit in each pump cycle. A motor is coupled to drive the pump mechanism. A controller is coupled to activate and deactivate the motor in alternation during each pump cycle with a duty cycle that varies within the pump cycle.

17 Claims, 9 Drawing Sheets

U.S. PATENT DOCUMENTS

| | | | |
|---|---|---|---|
| 5,152,680 A | 10/1992 | Okada | |
| 5,165,874 A | 11/1992 | Sancoff et al. | |
| 5,213,483 A | 5/1993 | Flaherty et al. | |
| 5,222,946 A | 6/1993 | Kamen | |
| 5,257,978 A | 11/1993 | Haber et al. | |
| 5,290,158 A | 3/1994 | Okada | |
| 5,395,320 A | 3/1995 | Padda et al. | |
| 5,429,485 A | 7/1995 | Dodge | |
| 5,499,969 A | 3/1996 | Beuchat et al. | |
| 5,509,439 A | 4/1996 | Tantardini | |
| 5,527,295 A | 6/1996 | Wing | |
| 5,575,309 A | 11/1996 | Connell | |
| 5,577,891 A | 11/1996 | Loughnane et al. | |
| 5,593,134 A * | 1/1997 | Steber et al. | 251/129.17 |
| 5,658,252 A | 8/1997 | Johnson | |
| 5,683,233 A | 11/1997 | Moubayed et al. | |
| 5,782,805 A | 7/1998 | Meinzer et al. | |
| 5,807,322 A | 9/1998 | Lindsey et al. | |
| 5,896,076 A | 4/1999 | Van Namen | |
| 5,924,852 A * | 7/1999 | Moubayed et al. | 417/474 |
| 5,996,964 A | 12/1999 | Ben-Shalom | |
| 6,095,189 A | 8/2000 | Ben-Shalom | |
| 6,164,921 A | 12/2000 | Moubayed et al. | |
| 6,165,874 A | 12/2000 | Powell et al. | |
| 6,203,296 B1 | 3/2001 | Ray et al. | |
| 6,261,262 B1 | 7/2001 | Briggs et al. | |
| 6,339,410 B1 | 1/2002 | Milner et al. | |
| 6,371,732 B1 * | 4/2002 | Moubayed et al. | 417/44.1 |
| 6,450,773 B1 | 9/2002 | Lipton | |
| 6,537,244 B2 | 3/2003 | Paukovits et al. | |
| 6,692,241 B2 | 2/2004 | Watanabe et al. | |
| 6,733,476 B2 * | 5/2004 | Christenson et al. | 604/151 |
| 7,018,361 B2 | 3/2006 | Gillespie, Jr. et al. | |
| 7,022,075 B2 | 4/2006 | Grunwald et al. | |
| 7,122,026 B2 | 10/2006 | Rogers et al. | |
| 7,163,385 B2 | 1/2007 | Gharib et al. | |
| 7,556,481 B2 * | 7/2009 | Moubayed | 417/477.3 |
| 7,762,795 B2 * | 7/2010 | Moubayed | 417/477.3 |
| 8,029,253 B2 * | 10/2011 | Rotem et al. | 417/478 |
| 2002/0156402 A1 | 10/2002 | Woog et al. | |
| 2002/0165503 A1 | 11/2002 | Morris et al. | |
| 2003/0040700 A1 | 2/2003 | Hickle et al. | |
| 2003/0182586 A1 | 9/2003 | Numano | |
| 2004/0181314 A1 | 9/2004 | Zaleski | |
| 2004/0191112 A1 * | 9/2004 | Hill et al. | 422/3 |
| 2005/0088409 A1 | 4/2005 | Van Berkel | |
| 2006/0051218 A1 | 3/2006 | Harttig | |
| 2007/0269324 A1 | 11/2007 | Goldor et al. | |
| 2008/0095649 A1 | 4/2008 | Ben-Shalom et al. | |
| 2008/0145249 A1 * | 6/2008 | Smisson et al. | 417/474 |
| 2009/0221964 A1 * | 9/2009 | Rotem et al. | 604/151 |
| 2009/0240201 A1 * | 9/2009 | Rotem et al. | 604/151 |
| 2009/0317268 A1 * | 12/2009 | Rotem et al. | 417/53 |
| 2010/0036322 A1 * | 2/2010 | Rotem | 604/151 |
| 2011/0152772 A1 * | 6/2011 | Rotem et al. | 604/153 |
| 2011/0152831 A1 * | 6/2011 | Rotem et al. | 604/506 |

FOREIGN PATENT DOCUMENTS

| | | | |
|---|---|---|---|
| EP | 0225158 A2 | 6/1987 | |
| FR | 2632529 A | 12/1989 | |
| JP | 60043188 A | 3/1985 | |
| JP | 6-169992 A | 6/1994 | |
| JP | 2002-57738 A | 2/2002 | |
| JP | 2004141418 A | 5/2004 | |
| WO | 9116933 A1 | 11/1991 | |
| WO | 03027503 A1 | 4/2003 | |
| WO | 2008059492 A2 | 5/2008 | |
| WO | 2008059493 A2 | 5/2008 | |
| WO | 2008059494 A2 | 5/2008 | |
| WO | 2008059495 A2 | 5/2008 | |
| WO | 2008059496 A2 | 5/2008 | |
| WO | 2008059498 A2 | 5/2008 | |
| WO | 2008059499 A2 | 5/2008 | |
| WO | 2008130644 A1 | 10/2008 | |

OTHER PUBLICATIONS

International Application PCT/IL2007/001398 Search Report dated Jun. 11, 2008.
International Application PCT/IL2007/001398 Patentability Report dated May 28, 2009.
International Application PCT/IL2007/001399 Search Report dated Jun. 4, 2008.
International Application PCT/IL2007/001399 Patentability Report dated May 19, 2009.
International Application PCT/IL2007/001400 Search Report dated Jul. 15, 2008.
International Application PCT/IL2007/001400 Patentability Report dated May 28, 2009.
International Application PCT/IL2007/001401 Search Report dated Sep. 24, 2008.
International Application PCT/IL2007/001401 Patentability Report dated May 28, 2009.
International Application PCT/IL2007/001402 Search Report dated Jun. 20, 2008.
International Application PCT/IL2007/001402 Patentability Report dated May 28, 2009.
International Application PCT/IL2007/001404 Search Report dated Jul. 14, 2008.
International Application PCT/IL2007/001404 Patentability Report dated May 28, 2009.
International Application PCT/IL2007/001405 Search Report dated Jul. 21, 2008.
International Application PCT/IL2007/001405 Patentability Report dated May 28, 2009.
International Application PCT/IL2005/001249 Search Report dated Apr. 5, 2006.
International Application PCT/IL2003/000947 Search Report dated Mar. 3, 2004.
Chinese Patent Application No. 200580045471.3 "Finger-type peristaltic pump" Official Action dated Jul. 18, 2008.
U.S. Appl. No. 09/125,438 Official dated Jul. 15, 1999.
U.S. Appl. No. 09/125,438 Official dated May 3, 1999.
European Application No. 05810500.8 Official Action dated Jul. 6, 2009.
International Application PCT/IL1997/000289 Search report dated Jan. 27, 1998.
International Application PCT/IL1997/000290 Search Report dated Jan. 27, 1998.
Rotem et al., U.S. Appl. No. 12/644,027, "Peristaltic Pump with Bi-Directional Pressure Sensor", Filed on Dec. 22, 2009.
Honeywell Sensing and Control, "FSS1500NSB force sensor", Golden Valley, Minnesota, USA, 1998-2004 http://sccatalog.honeywell.com/imc/printfriendly.asp?FAM=force&PN=FSS1500NSB.
U.S. Appl. No. 12/464,202 Official Action dated Oct. 3, 2011.
U.S. Appl. No. 12/463,399 Official Action dated Jul. 21, 2011.
U.S. Appl. No. 12/514,310 Official Action dated Jul. 21, 2011.
Chinese Patent Application No. 200780041966.8 Official Action dated Jul. 13, 2010.
U.S. Appl. No. 11/791,599 Official dated Aug. 19, 2010.
U.S. Appl. No. 12/514,311 Official dated Sep. 16, 2010.
U.S. Appl. No. 12/644,027 Official Action dated Apr. 28, 2011.
U.S. Appl. No. 11/791,599 Official Action dated Mar. 31, 2011.
European Patent Application # 10192477.7 Search Report dated May 10, 2011.

* cited by examiner

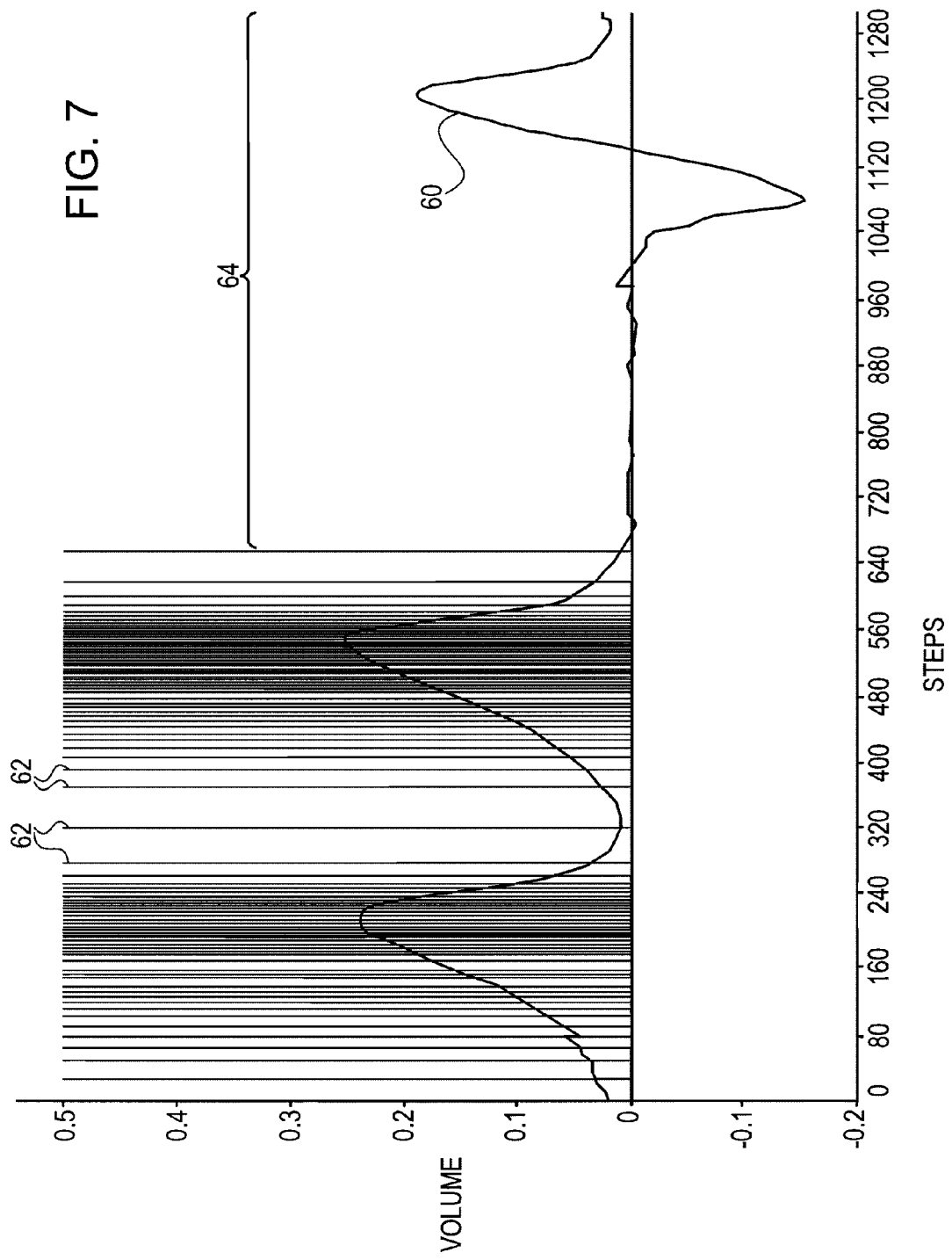

PERISTALTIC PUMP WITH LINEAR FLOW CONTROL

FIELD OF THE INVENTION

The present invention relates generally to medical devices, and specifically to infusion pumps.

BACKGROUND OF THE INVENTION

Various types of medical infusion pumps are known in the art. One common type of infusion pump is a peristaltic pump, in which fluid is made to flow through an elastic tube by external compression of the tube. Typically, a peristaltic mechanism, such as a set of cams or fingers, compresses the tube in a cyclic pattern at a sequence of locations along the length of the tube, so as to cause the fluid to flow through the tube at a desired volumetric rate. Peristaltic infusion pumps are described, for example, in U.S. Pat. Nos. 5,290,158, 5,395,320, and 5,807,322, as well as in U.S. Patent Application Publications 2007/0269324, 2009/0221964 and 2009/0240201, and in PCT International Publication WO 2008/059496. The disclosures of all of these cited patents and publications are incorporated herein by reference.

SUMMARY OF THE INVENTION

Peristaltic infusion pumps may operate by cyclically compressing and releasing a flexible tube containing a fluid at multiple different locations and different times. Consequently, the rate of fluid output from the tube, and hence of fluid delivery to the body of the patient to whom the tube is connected, may tend to vary within each cycle of the pump. At high fluid delivery rates, this variation may not be clinically significant; but the inventors have discovered that the variation in the output at low flow rates, which are typical in delivery of certain medications, for example, can cause undesirable fluctuations in the rate at which the fluid is delivered to the patient.

There is therefore provided, in accordance with an embodiment of the present invention, a peristaltic pump, including a conduit having a first end for receiving a fluid from a reservoir and a second end for delivering the fluid. A plurality of fingers are disposed at respective locations along a segment of the conduit and are configured to alternately compress and release the conduit at the locations. A cyclical pump mechanism is coupled to move the fingers between respective compressed and released positions in a spatio-temporal pattern so as to drive a predetermined quantity of the fluid through the segment of the conduit in each pump cycle. A motor is coupled to drive the pump mechanism. A controller is coupled to activate and deactivate the motor in alternation during each pump cycle with a duty cycle that varies within the pump cycle.

In some embodiments, the pump cycle is characterized by a variation in a quantity of the fluid that is delivered per step of the motor during the pump cycle, and the controller is operative to modulate the duty cycle so that the quantity of the fluid that is delivered through the conduit per unit time over the pump cycle is constant. The controller may be operative to activate and deactivate the motor by applying a waveform with a fixed period to the motor while varying a duration during which the motor is on during each period. In a disclosed embodiment, the pump cycle typically has first and second parts, such that the predetermined quantity of the fluid is driven through the segment during the first part, and the controller is operative to drive the motor so as to cause the pump mechanism to complete the second part of the pump cycle during a single period of the waveform.

In disclosed embodiments, the controller is operative to activate and deactivate the motor by applying a waveform to the motor, and to adjust a flow rate through the conduit by modifying a characteristic of the waveform. The characteristic may be selected from a group of characteristics consisting of an average duty cycle of the waveform, a period of the waveform, and a number of steps of the motor per period of the waveform. Typically, the controller is operative to activate and deactivate the motor in alternation to generate flow rates below a certain minimum level, and to run the motor continuously to generate flow rates above the minimum level.

In some embodiments, the conduit includes an elastic material, which exerts a first force against the fingers in response to compression of the conduit by the fingers, and the fingers include magnets, and the pump includes a ferromagnetic frame, which exerts a second force on the magnets, opposite to and balancing the first force during the pump cycle. In one embodiment, the pump mechanism includes a camshaft, which is coupled to be driven by the motor and includes multiple cams, each configured to drive a respective finger and having a crescent-shaped design for enhancing the balancing of the forces.

In a disclosed embodiment, the pump includes a rotation sensor, which is configured to measure an angle of rotation of the motor and to provide feedback to the controller regarding the rotation of the motor.

There is also provided, in accordance with an embodiment of the present invention, a method for fluid delivery, including providing a peristaltic infusion pump including a cyclical pump mechanism and a motor coupled to drive the pump mechanism. The pump is driven to deliver a fluid by activating and deactivating the motor in alternation during each pump cycle with a duty cycle that varies within the pump cycle.

There is additionally provided, in accordance with an embodiment of the present invention, a peristaltic pump having a pump cycle and including a conduit, including an elastic material, having a first end for receiving a fluid from a reservoir and a second end for delivering the fluid. A plurality of fingers, which include magnets, are disposed at respective locations along a segment of the conduit and are configured to alternately compress and release the conduit at the locations, whereby the conduit exerts a first force against the fingers in response to compression of the conduit. A ferromagnetic frame exerts a second force on the magnets, opposite to and balancing the first force during the pump cycle. A cyclical pump mechanism is coupled to move the fingers between respective compressed and released positions in a spatio-temporal pattern so as to drive a predetermined quantity of the fluid through the segment of the conduit in each pump cycle. A motor is coupled to drive the pump mechanism. A controller is coupled to activate and deactivate the motor in alternation during each pump cycle with a duty cycle that varies within the pump cycle.

The present invention will be more fully understood from the following detailed description of the embodiments thereof, taken together with the drawings in which:

BRIEF DESCRIPTION OF THE DRAWINGS

FIG. 7 is a plot showing a variation in fluid output over a pump cycle, in accordance with an embodiment of the present invention;

DETAILED DESCRIPTION OF EMBODIMENTS

Figure 1:
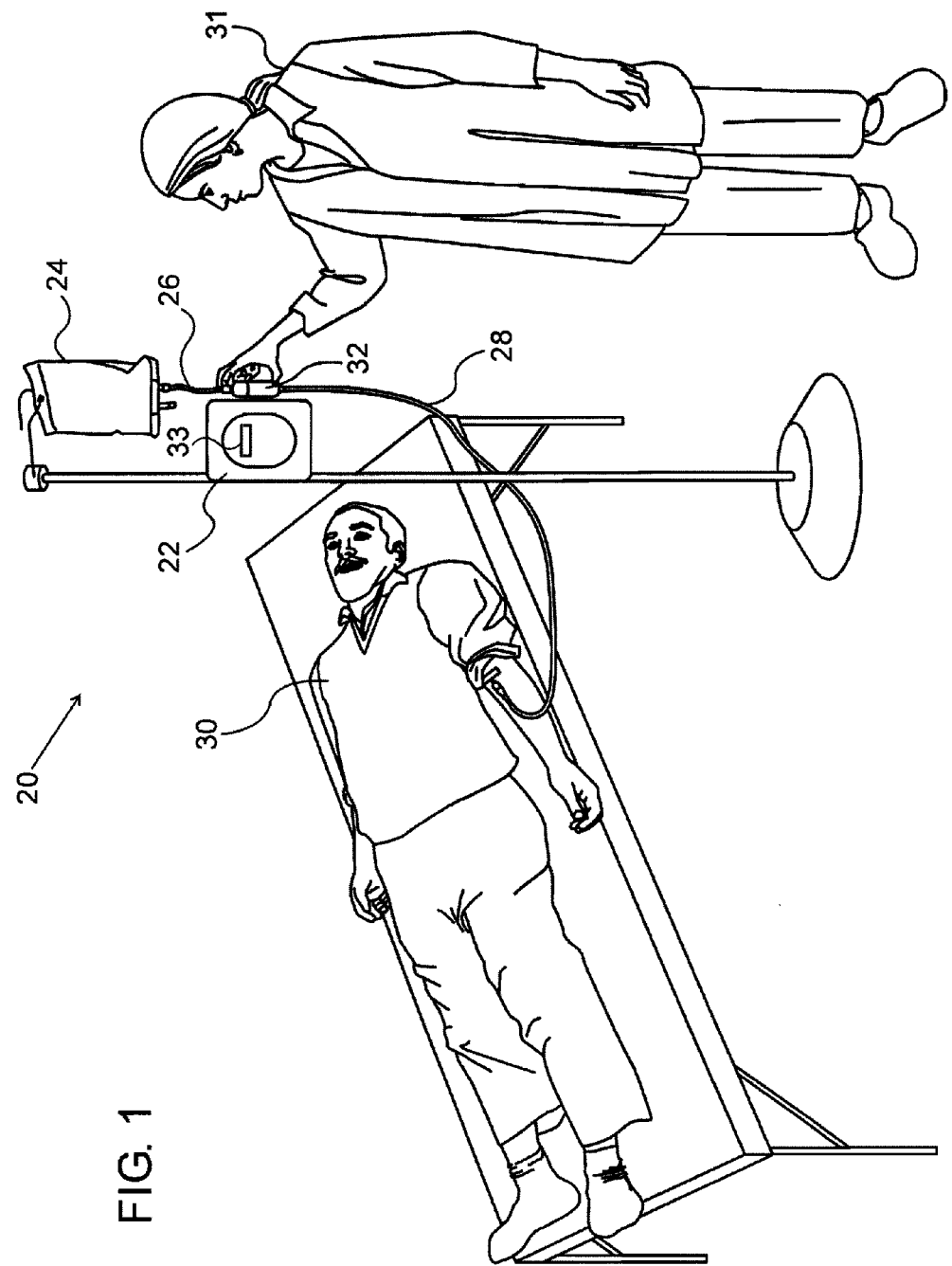
FIG. 1 is a schematic, pictorial illustration of a medical infusion system, in accordance with an embodiment of the present invention.

FIG. 1 is a schematic, pictorial illustration of a medical infusion system 20, in accordance with an embodiment of the present invention. System 20 comprises a peristaltic infusion pump 22, which may pump an infusion fluid from a reservoir 24, through an upstream tube segment 26 (commonly referred to as the "supply line") and a downstream tube segment 28 (commonly referred to as the "patient line"), into a vein of a patient. This particular type of infusion system is shown here by way of illustration, but the principles of the present invention, as described hereinbelow, may likewise be applied to other types of peristaltic pumps and in substantially any sort of application that uses such pumps, particularly in delivery of drugs. Although the pictured embodiment represents a clinical environment, the devices and methods described herein are also suitable for ambulatory and home use.

Tube segments 26 and 28 may be connected to a mechanical interface unit 32, which couples to pump 22 in a manner that is shown and explained below in greater detail. Unit 32 contains a conduit (not shown in FIG. 1) that is connected in series with tube segments 26 and 28, thus defining a flow path from reservoir 24 to patient 30. Unit 32 in this embodiment may be constructed so as to enable an operator 31 to connect the unit to pump 22 stably and reliably by fitting the unit against the pump and snapping it into place. The operator may set the desired rate of fluid delivery to the patient, typically via a user interface 33 of the pump. A pump controller (as shown in the figures that follow) may then regulate the operation of the pump motor automatically in order to achieve the desired rate.

Figure 2:
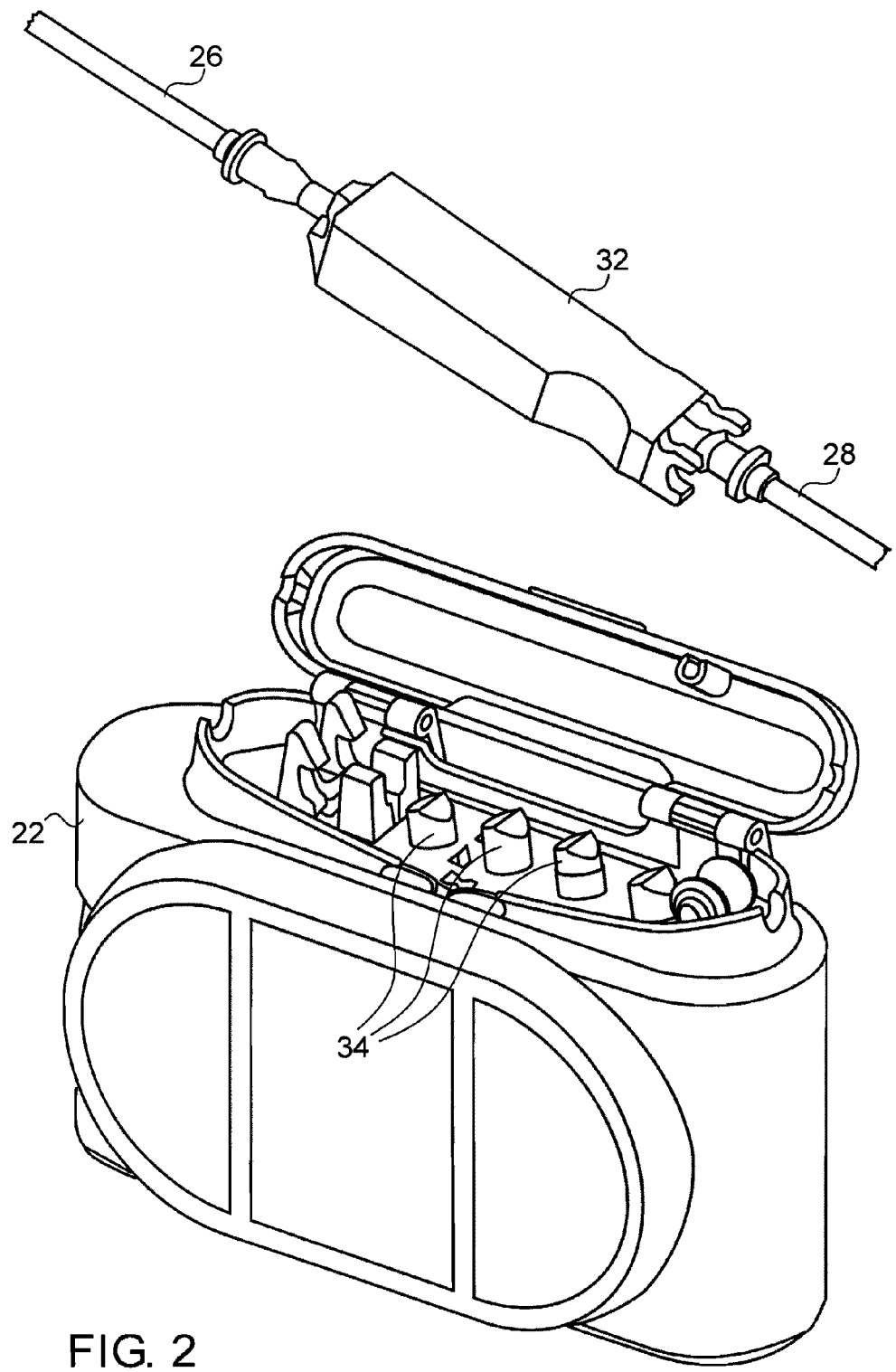
FIG. 2 is a schematic, pictorial illustration showing external details of an infusion pump, in accordance with an embodiment of the present invention.

FIG. 2 is a schematic, pictorial illustration showing external details of infusion pump 22, in accordance with an embodiment of the present invention. Mechanical interface unit 32 may bring a segment of conduit into contact with a peristaltic mechanism comprising multiple fingers 34. The fingers may move up and down to compress and release the conduit in a predetermined cyclic pattern, so as to propel fluid downstream from tube segment 26 to tube segment 28. Details of the mechanical interface unit and its attachment to the pump are described in the above-mentioned U.S. Patent Application Publication 2009/0221964.

Figure 3:
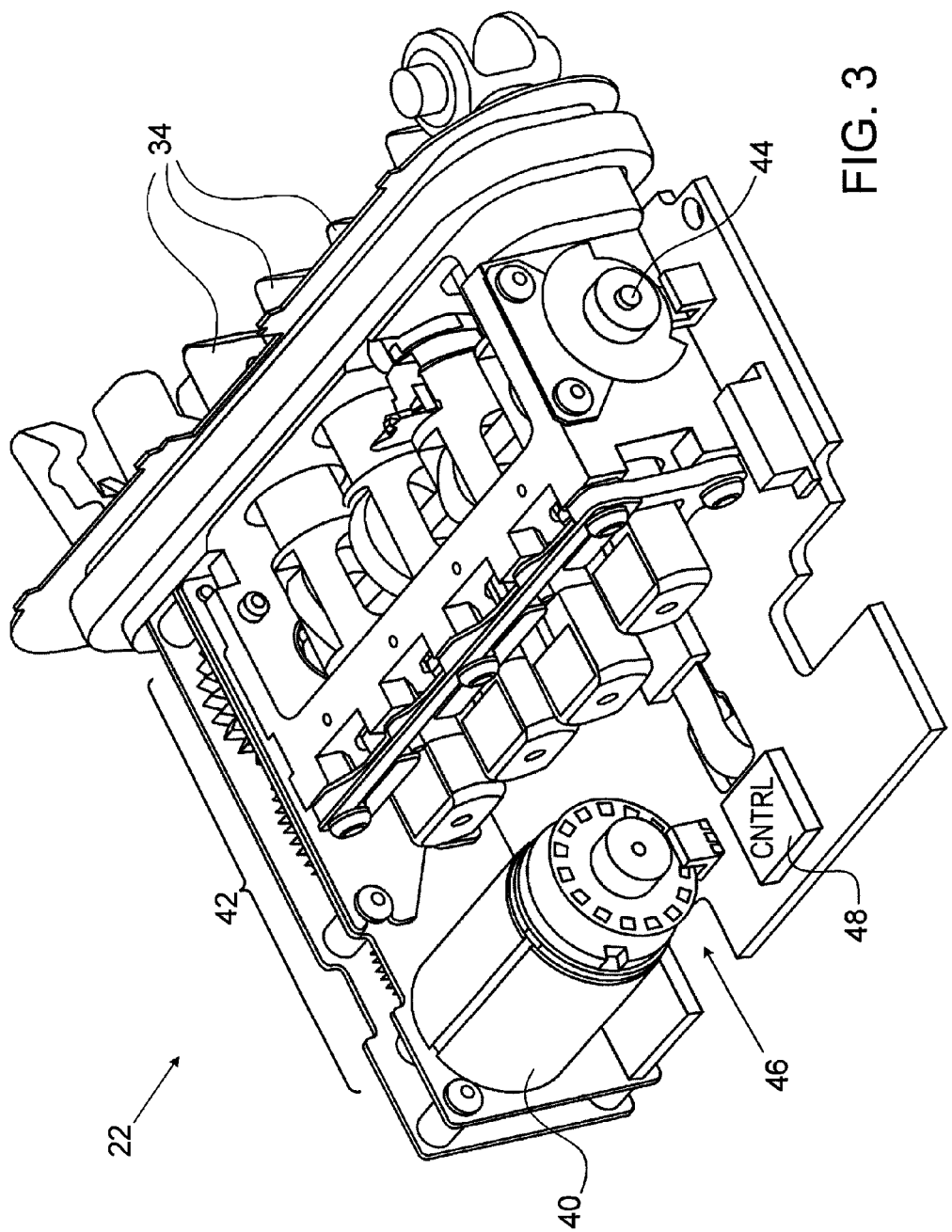
FIG. 3 is a schematic, pictorial illustration showing internal details of an infusion pump, in accordance with an embodiment of the present invention.
Figure 4:
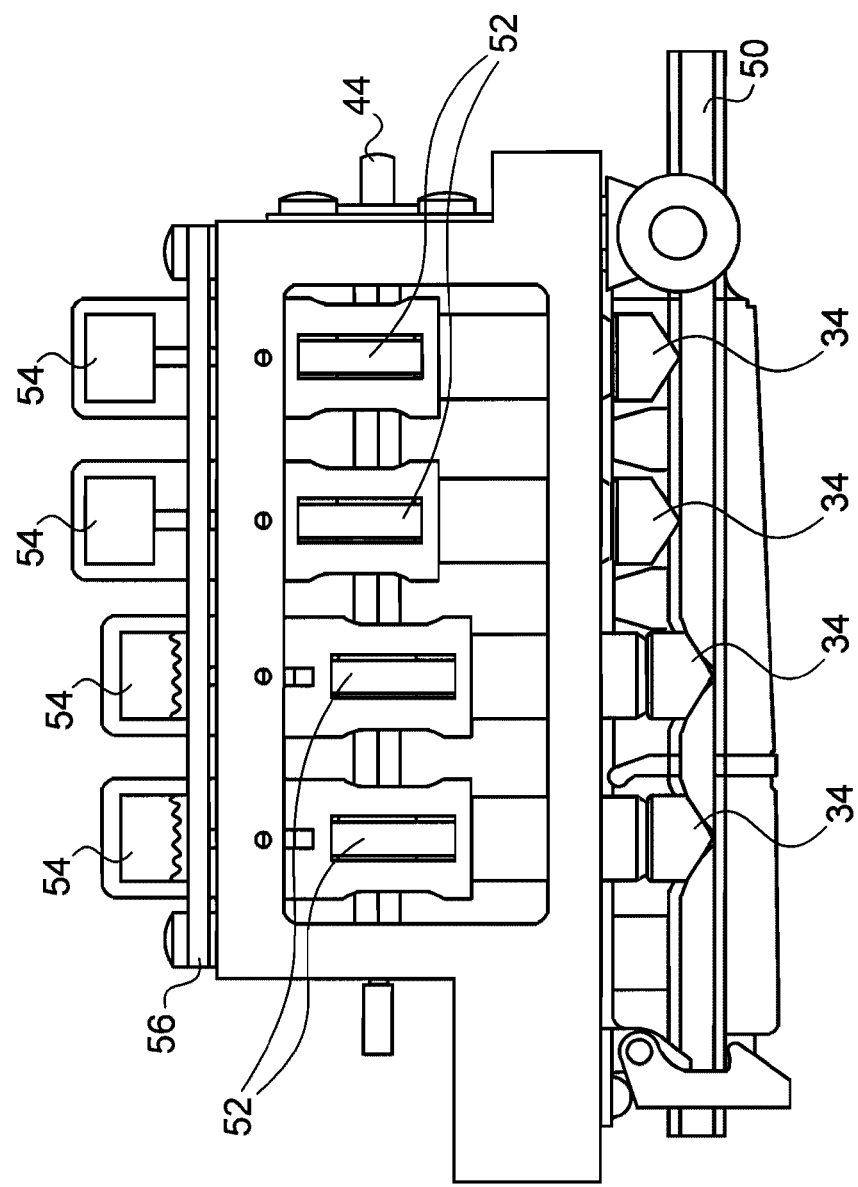
FIG. 4 is a schematic side view of a peristaltic assembly in an infusion pump, in accordance with an embodiment of the present invention.

Reference is now made to FIGS. 3 and 4, which schematically show internal details of the pump mechanism in infusion pump 22, in accordance with an embodiment of the present invention. FIG. 3 is an isometric pictorial illustration, while FIG. 4 is a side view. A motor 40, such as a Maxon RE-max17 DC motor (produced by Maxon Motor, Sachseln, Switzerland), may drive fingers 34 via a geared transmission 42 (such as the GX gear, also produced by Maxon Motor), which may turn a camshaft 44. The camshaft may turn multiple cams 52, each of which may operate a respective finger 34. The phases of the cams may be arranged so that the fingers alternately compress and release conduit 50 in a predefined spatio-temporal pattern in order to move fluid through the conduit, as described in further detail hereinbelow.

A controller 48 activates and deactivates motor 40, typically (although not necessarily) by switching power on and off to the motor, in order to regulate the rate of fluid flow through conduit 50. Optionally, the gear ratio of transmission 42 may also be varied, either by the controller or by manual operation, in order to provide a selection of different speed ranges, according to the desired rate of flow. An encoder 46 may measure the angle of rotation of the motor, and thus provide feedback to controller 48 regarding the rotation of the motor. The encoder shown in the figure is of the type comprising a wheel with windows and a light source and sensor to translate the wheel position to an electrical signal. Alternatively, any other suitable rotation sensor may be used. For accurate flow control, transmission 42 may typically have a high gear ratio, in the range of 20-25:1, for example, and encoder 46 provides high angular resolution, with as many as 1000-1500 control points per revolution of camshaft 44. In the present example, there are 1308 encoder control points per camshaft rotation (based on 21.8 motor cycles to each shaft cycle and fifteen windows in the encoder wheel, wherein each window provides four location information points). These features of the pump, together with the novel control methods described hereinbelow, enable pump 22 to achieve a dynamic range on the order of 10,000:1, with accurately-controlled continuous flow from less than 0.5 ml/h to several liters per hour.

Controller 48 typically comprises an off-shelf microcontroller, such as a Microchip PIC18F8720 device (produced by Microchip Technology Inc., Chandler, Ariz.), with suitable interfaces to motor 40 and encoder 46 (and possibly to other components of pump, such as safety interlocks). The microcontroller may be programmed in software or firmware to carry out the flow control functions that are described herein. Alternatively, some or all of the functions of controller may be implemented using dedicated or programmable hardware logic circuits.

Figure 5:
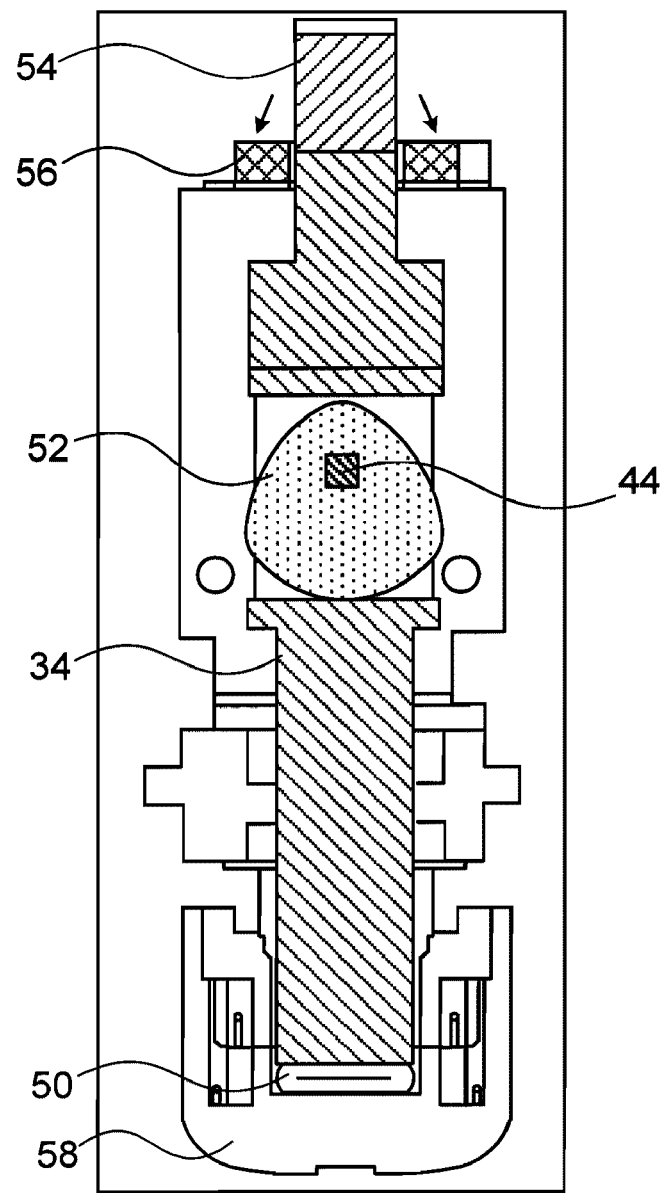
FIG. 5 is a schematic sectional view of a finger in the peristaltic assembly of FIG. 4, in accordance with an embodiment of the present invention.

FIG. 5 is a schematic sectional view of one finger 34 in the peristaltic assembly of FIG. 4, in accordance with an embodiment of the present invention. In this view, finger 34 may compress conduit 50 against a base 58 (which in practice may be the body of housing 32, as shown in FIG. 2). As camshaft 44 turns cam 52, the cam may lift finger 34, thus releasing the conduit at the location under the finger.

Each finger 34 may comprise a respective magnet 54, which interacts with a ferromagnetic frame 56 that may be fixed to the pump chassis. The strength and mechanical configuration of magnets 54 may be chosen so that the magnetic attraction between the magnets and frame 56 is just slightly stronger than the oppositely-directed elastic forces engendered by the squeezing of conduit 50 by finger 34 when compressing the conduit. (The conduit typically comprises an elastic material such as silicone.) The magnetic and elastic forces are thus balanced, so that the power demands on motor 40 in driving camshaft 44 are minimized. Examples of magnetic balancing are described in the above-mentioned U.S.

Patent Application Publication 2009/0240201 and PCT International Publication WO 2008/059496.

When pump 22 is operating at low flow rates, below a certain minimum level, controller 48 may activate and deactivate motor 40 in alternation, as explained in detail hereinbelow. The magnetically-balanced design of fingers 34 that is shown in FIGS. 4 and 5 may be particularly advantageous in this context, since it may permit the motor to start rotation of the camshaft with low power input. Furthermore, because of the magnetic balancing, the pump mechanism may develop only minimal inertia while it is in motion, and may therefore stop immediately (due to the small amount of friction that exists in the mechanism) and hold its position stably when the motor stops. Cams 52 may have an oblong shape or a special crescent-shaped design. The special crescent-shaped cams may enhance the magnetic balancing by extending the range of rotation of the camshaft over which the corresponding finger holds conduit 50 closed. This design may provide additional mechanical tolerance and may facilitate the low-power start and stable stop of the mechanism that are described above. Exemplary cam designs are described further in the above-mentioned U.S. and PCT publications. With the sort of mechanical and magnetic design that is shown in FIGS. 3-5, for example, the inventors have found it possible to run pump 22 on an internal battery at an intermediate flow rate (125 ml/h, for example) for more than 32 hours.

Figure 6:
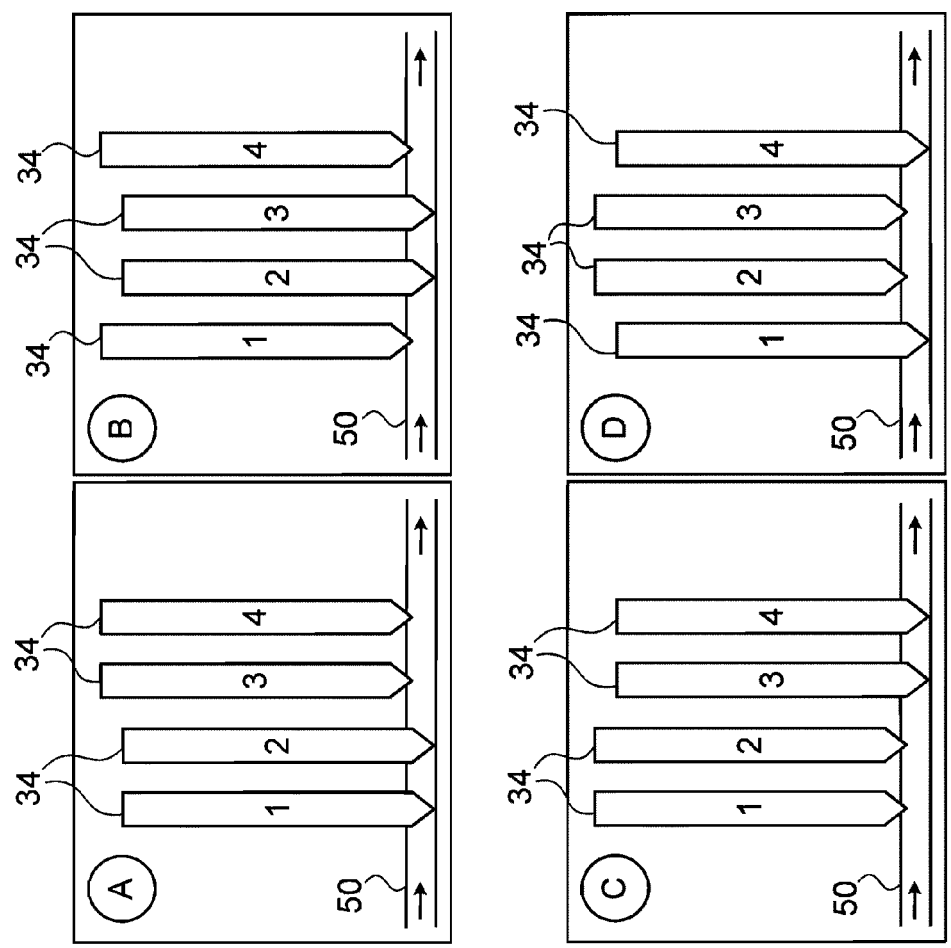
FIGS. 6A-6D are schematic side views of a set of fingers in a peristaltic assembly, showing a spatio-temporal pattern of movement of the fingers, in accordance with an embodiment of the present invention.

FIGS. 6A-6D are schematic side views of fingers 34 in pump 22, showing the cyclic spatio-temporal pattern of movement of the fingers, in accordance with an embodiment of the present invention. These figures present the state of each finger at each of the four steps of a single pump cycle. At each step, two of the fingers are static and two are moving, in accordance with the positions of the respective cams. In each of the two steps represented by FIGS. 6B and 6C, a single drop of fluid may be forced out of the downstream end of conduit 50. In FIGS. 6A and 6D, on the other hand, there may be substantially no fluid output. The volume of fluid output per cycle depends on the dimensions of the pump mechanism and the conduit. In typical medical applications, the volume per cycle is typically 50-350 µl.

FIG. 7 is a plot 60 showing the variation in the volume of fluid output from pump 22 over a pump cycle, in accordance with an embodiment of the present invention. The plot shows the volume output per step of motor 40, as measured by encoder 46, for each of 1308 steps (corresponding to multiple rotations of motor 40) in a single cycle of the pump. Equivalently, the steps may be seen as angular divisions (0.275° in this example) in a rotation of camshaft 44 that corresponds to a single pump cycle. The two peaks at the left of the figure correspond to the two drops that are output per cycle, while the single sawtooth waveform at the right of the figure is a flow artifact that does not result in any significant fluid output.

For high flow rates (above about 399 ml/h, for example), with pump 22 operating at multiple cycles/sec (for example, above 108 cycles/min), the non-uniform output of pump 22 over each pump cycle averages out into a substantially continuous flow. It is therefore possible to operate motor 40 continuously at the appropriate speed to give the desired flow rate. On the other hand, at very slow speeds, the pump may make less than one cycle per minute (and as few as 1.8 cycles/hour for a flow rate of 0.1 ml/h), and the non-linear variation in fluid output over time will therefore be significant and may be clinically undesirable, particularly in delivery of drugs that require a constant infusion rate.

In embodiments of the present invention, in order to accurately control the fluid output at low and medium flow rates, the non-linear shape of plot 60 may be linearized by controlling the duty cycle of motor 40. The term "duty cycle," as used in the context of the present patent application and in the claims, is used in the conventional sense to mean the fraction of time in which the motor is in its active state, i.e., the fraction of time during which the motor is in motion. For this purpose, each pump cycle is divided into a fixed number of intervals 62, such as 196 intervals, each giving the same fluid output volume (roughly 0.3 µl per interval in the present example, in which the entire pump cycle gives an output of 63 µl). Because of the non-uniformity of the fluid output as a function of motor rotation, however, the durations of intervals 62, in terms of motor steps, vary widely, as can be seen in the figure. The interval durations, thus, may be chosen so that the integral of plot 60 is equal over all intervals. The last interval in the cycle, referred to herein as a "rewind" interval 64, returns the pump quickly to the beginning of the next cycle.

When pump 22 is set to operate at a low or medium flow rate, controller 48 may activate and deactivate motor 40 at fixed periods, each period corresponding to one of intervals 62. The controller varies the duty cycle in each period (i.e., the amount of time during the period in which the motor is on), however, in proportion to the length of the corresponding interval. In other words, in each period, the motor may run for the exact amount of time needed to complete the steps in the corresponding interval, so that the fluid output of the pump during all periods in the cycle is effectively constant. (In the context of the present patent application and in the claims, the term "constant" is to be interpreted in the clinical sense, i.e., when the variations in the flow are clinically insignificant, the flow is considered to be constant.) The minimum length of the periods is limited by the length of rewind interval 64: The periods should be long enough to permit the motor to cycle through all of the steps in the rewind interval (654 steps in the present example) within a single period. Above this limit, either the period or the average duty cycle, or both, may be adjusted linearly in order to give the desired output flow rate.

Figure 8A:
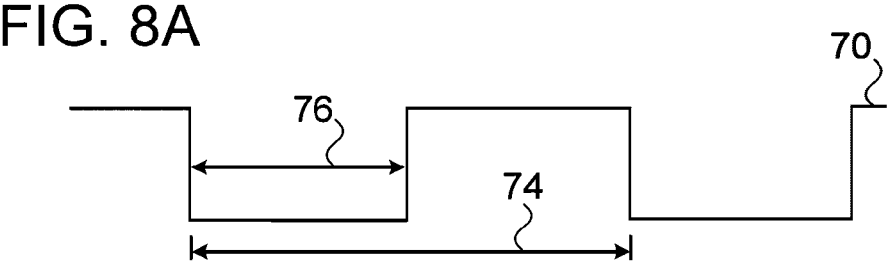
FIGS. 8A-8C are plots that schematically show pump control waveforms, in accordance with an embodiment of the present invention.
Figure 8B:
Figure 8C:
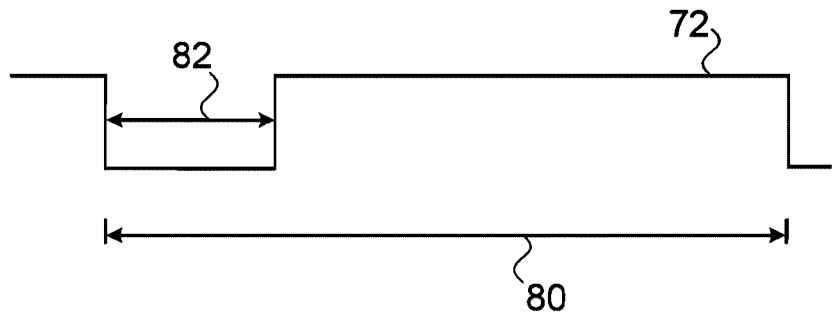

FIGS. 8A-8C are plots that schematically show pump control waveforms 70, 72, in accordance with an embodiment of the present invention. The waveforms are output from controller 48 to motor 40 in order to turn the motor off with the appropriate duty cycle, wherein in the present examples, the motor runs while the waveform is at its low value and stops when the waveform is at the high value.

FIGS. 8A and 8B show the same waveform 70 at different intervals within a pump cycle at a certain fixed period 74 per interval. FIG. 8A shows the waveform in a low-flow segment of plot 60 (FIG. 7), in the neighborhood of step 80, for example. At this point in the pump cycle, the motor may be driven with a long pulse duration 76, in proportion to the length of the corresponding interval 62. FIG. 8B, on the other hand, shows the waveform near the peak of plot 60, with a short pulse duration 78 corresponding to the short duration of the interval at step 200, for example. The duty cycle may be defined, in each period, as the ratio of the pulse duration to period 74. In between the values shown in FIGS. 8A and 8B, the duty cycle may gradually decrease, and may then grow again beyond the peak.

In FIG. 8C, waveform 72 has a longer period 80, but is assumed to have the same number of motor steps and on/off intervals per pump cycle as in FIGS. 8A and 8B. Therefore, assuming pulse duration 82 is comparable to the pulse duration for the corresponding interval in waveform 70, waveform 72 may have a lower average duty cycle, and pump 22 may thus have a lower fluid output rate when motor is driven by waveform 72 than by waveform 70. For example, if period 80 is twice period 74, while the pulse durations remain the same, waveform 72 may have half the average duty cycle of waveform 70, and the pump output may therefore be reduced by half, as well. On the other hand, the average duty cycle, as well as the period, may be varied in order to give other fluid output rates, while still keeping up a linear, constant output during each pump cycle by maintaining the duty cycle variation from period to period that is indicated by intervals 62.

As another alternative, controller 48 may change the number of intervals per pump cycle. For example, each pump cycle may be divided into 98 intervals, instead of 196, meaning that each period in the waveform driving motor 40 may include twice the number of motor steps as a corresponding period in the preceding scheme. Changing the number of intervals per pump cycle is conceptually equivalent to changing the "gear" of the transmission, and provides additional flexibility in setting the range of fluid output rates from pump 22.

Figure 9:
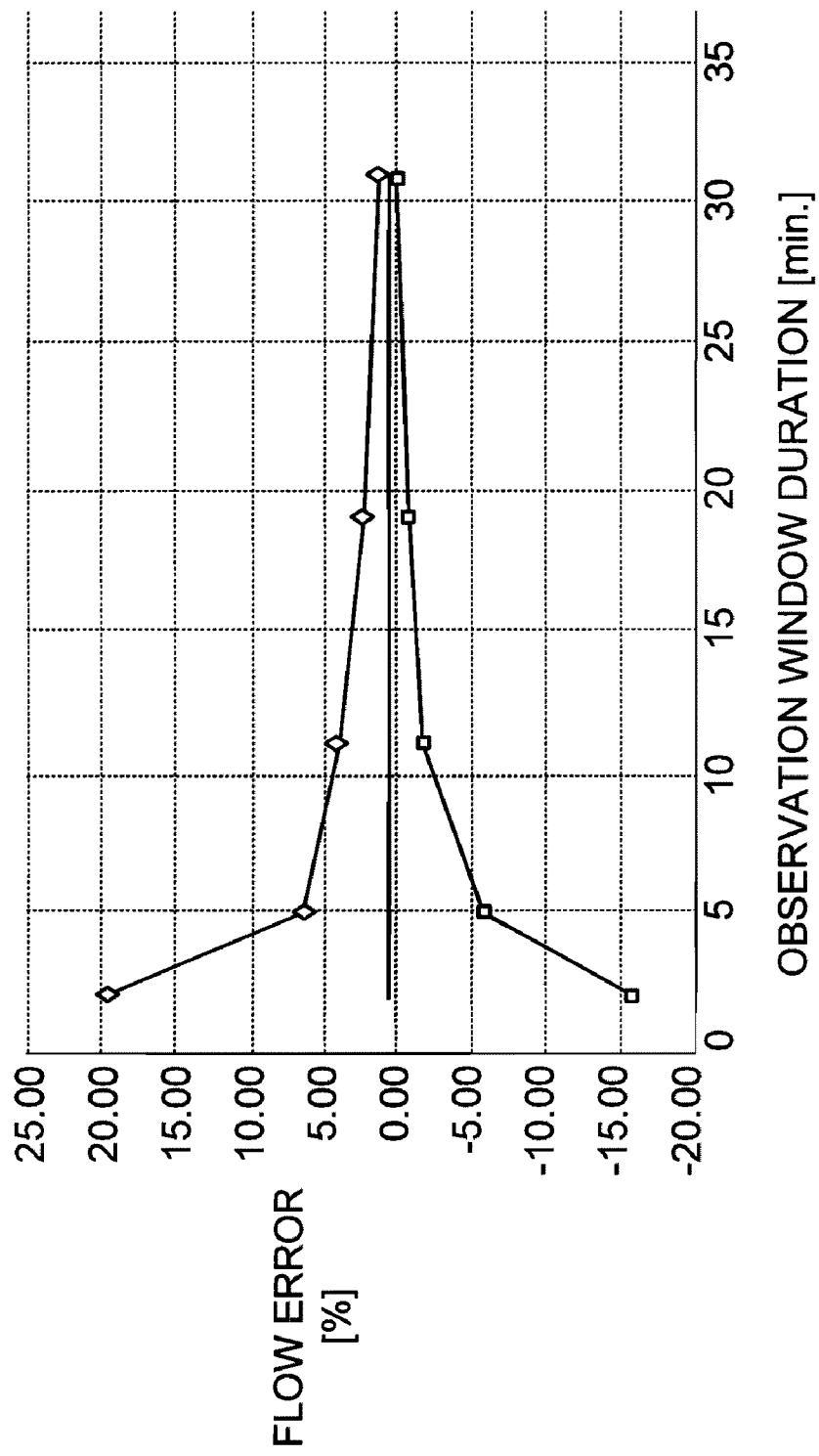
FIG. 9 is a trumpet plot, which schematically shows flow error in fluid delivery by a peristaltic pump, in accordance with an embodiment of the present invention.

FIG. 9 is a trumpet plot, which schematically shows flow error in fluid delivery by pump 22, in accordance with an embodiment of the present invention. "Error" in this context means the variation in the flow volume over a given observation window. To compute this error, the fluid output from the pump is measured over many windows of the same duration at different points in time over the course of a test run of the pump, the measurements are averaged, and the maximum deviation between measurements is recorded. Different window durations are also tested. It is to be expected that the error will be low over long window durations, since fluctuations in the flow rate tend to average out over time. On the other hand, when the pump is operated at a low flow rate, in which each cycle of the pump can take as long as several minutes, the large fluctuations in pump output that are seen in plot 60 (FIG. 7) are liable to cause substantial error.

The results shown in FIG. 9 demonstrate the effectiveness of the nonlinear drive mechanism described above in counteracting the flow rate fluctuations and providing an effectively constant pump output. The figure presents actual experimental results measured at a nominal pump output rate of 0.5 ml/h. For short observation windows (1 min), the maximum variation in measured flow may be in the range of 15-20%. For a five-minute window, the variation may drop to 5% and may continue to decrease with longer window length. In clinical terms, these results may show that pump 22 is capable of maintaining a nearly constant, continuous dosage of drug delivery to the patient, even at very low flow rates. At higher flow rates, the error bounds may be considerably smaller.

Although the embodiments described above relate, for the sake of clarity, specifically to the design of pump 22, the principles of the present invention may similarly be applied in controlling the operation of other peristaltic pumps, for both medical and non-medical applications. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A peristaltic pump, comprising:
   a conduit having a first end for receiving a fluid from a reservoir and a second end for delivering the fluid;
   a plurality of fingers, which are disposed at respective locations along a segment of the conduit and are configured to alternately compress and release the conduit at the locations;
   a cyclical pump mechanism, which is coupled to move the fingers between respective compressed and released positions in a spatio-temporal pattern so as to drive a predetermined quantity of the fluid through the segment of the conduit in each pump cycle, wherein said cyclical pump mechanism is characterized by a non-linear flow to phase function;
   a motor, which is coupled to drive the pump mechanism; and
   a controller, which is coupled to activate and deactivate the motor in alternation during each pump cycle with a duty cycle that varies within the pump cycle to substantially compensate for the non-linear flow to phase function.

2. The pump according to claim 1, wherein the pump cycle is characterized by a variation in a quantity of the fluid that is delivered per step of the motor during the pump cycle, and wherein the controller is operative to modulate the duty cycle so that the quantity of the fluid that is delivered through the conduit per unit time over the pump cycle is constant.

3. The pump according to claim 2, wherein the controller is operative to activate and deactivate the motor by applying a waveform with a fixed period to the motor while varying a duration during which the motor is on during each period.

4. The pump according to claim 3, wherein the pump cycle has first and second parts, such that the predetermined quantity of the fluid is driven through the segment during the first part, and wherein the controller is operative to drive the motor so as to cause the pump mechanism to complete the second part of the pump cycle during a single period of the waveform.

5. The pump according to claim 1, wherein the controller is operative to activate and deactivate the motor by applying a waveform to the motor, and to adjust a flow rate through the conduit by modifying a characteristic of the waveform.

6. The pump according to claim 5, wherein the characteristic is selected from a group of characteristics consisting of an average duty cycle of the waveform, a period of the waveform, and a number of steps of the motor per period of the waveform.

7. The pump according to claim 5, wherein the controller is operative to activate and deactivate the motor in alternation to generate flow rates below a certain minimum level, and to run the motor continuously to generate flow rates above the minimum level.

8. The pump according to claim 1, wherein the conduit comprises an elastic material, which exerts a first force against the fingers in response to compression of the conduit by the fingers, and wherein the fingers comprise magnets, and the pump comprises a ferromagnetic frame, which exerts a second force on the magnets, opposite to and balancing the first force during the pump cycle.

9. The pump according to claim 8, wherein the pump mechanism comprises a camshaft, which is coupled to be driven by the motor and comprises multiple cams, each configured to drive a respective finger and having a crescent-shaped design for enhancing the balancing of the forces.

10. The pump according to claim 1, and comprising a rotation sensor, which is configured to measure an angle of rotation of the motor and to provide feedback to the controller regarding the rotation of the motor.

11. A method for fluid delivery, comprising:
   providing a peristaltic infusion pump comprising a cyclical pump mechanism wherein said cyclic pumping mechanism is characterized by a non-linear flow to phase function and a motor coupled to drive the pump mechanism; and driving the pump to deliver a fluid by activating and deactivating the motor in alternation during each pump cycle with a duty cycle that varies within the pump cycle to substantially compensate for the non-linear flow to phase function.

12. The method according to claim 11, wherein the pump cycle is characterized by a variation in a quantity of the fluid that is delivered per step of the motor during the pump cycle, and wherein driving the pump comprises modulating the duty cycle so that the quantity of the fluid that is delivered by the pump per unit time over the pump cycle is constant.

13. The method according to claim 12, wherein modulating the duty cycle comprises applying a waveform with a fixed period to the motor while varying a duration during which the motor is on during each period.

14. The method according to claim 11, wherein driving the pump comprises applying a waveform to the motor, and modifying a characteristic of the waveform in order to adjust a rate of flow of the fluid.

15. The method according to claim 14, wherein the characteristic is selected from a group of characteristics consisting of an average duty cycle of the waveform, a period of the waveform, and a number of steps of the motor per period of the waveform.

16. The method according to claim 11, wherein driving the pump comprises activating and deactivating the motor in alternation to generate flow rates below a certain minimum level, and running the motor continuously to generate flow rates above the minimum level.

17. A peristaltic pump having a pump cycle and comprising:
- a conduit, comprising an elastic material, having a first end for receiving a fluid from a reservoir and a second end for delivering the fluid;
- a plurality of fingers, which comprise magnets and are disposed at respective locations along a segment of the conduit and are configured to alternately compress and release the conduit at the locations, whereby the conduit exerts a first force against the fingers in response to compression of the conduit;
- a ferromagnetic frame, which exerts a second force on the magnets, opposite to and balancing the first force during the pump cycle;
- a cyclical pump mechanism, which is coupled to move the fingers between respective compressed and released positions in a spatio-temporal pattern so as to drive a predetermined quantity of the fluid through the segment of the conduit in each pump cycle, wherein said cyclical pump mechanism is characterized by a non-linear flow to phase function;
- a motor, which is coupled to drive the pump mechanism; and
- a controller, which is coupled to activate and deactivate the motor in alternation during each pump cycle with a duty cycle that varies within the pump cycle to substantially compensate for the non-linear flow to phase function.

* * * * *